United States Patent
Neto

(10) Patent No.: US 9,861,927 B2
(45) Date of Patent: Jan. 9, 2018

(54) INTRODUCED IN ADSORPTION FILTER FOR INHALED HALOGENATED ANESTHETICS FOR CARDIOPULMONARY CIRCULATION BYPASS

(71) Applicant: Copeen Treinamento e Consultoria em Anestesia EIRELI, San Paulo Capital (BR)

(72) Inventor: Caetano N. Neto, San Paulo Capital (BR)

(73) Assignee: Copeen Treinamento e Consultoria em Anestesia Eireli (BR)

( * ) Notice: Subject to any disclaimer, the term of this patent is extended or adjusted under 35 U.S.C. 154(b) by 98 days.

(21) Appl. No.: 15/154,163

(22) Filed: May 13, 2016

(65) Prior Publication Data

US 2017/0065925 A1    Mar. 9, 2017

(30) Foreign Application Priority Data

Sep. 9, 2015    (BR) .......................... 1020150220170

(51) Int. Cl.
   *B01D 53/04*    (2006.01)
   *A61M 1/16*    (2006.01)

(52) U.S. Cl.
   CPC ..... *B01D 53/0446* (2013.01); *B01D 53/0407* (2013.01); *A61M 1/1698* (2013.01);
   (Continued)

(58) Field of Classification Search
   CPC ............ B01D 53/0407; B01D 53/0446; B01D 2253/102; B01D 2257/20;
   (Continued)

(56) References Cited

U.S. PATENT DOCUMENTS 3,941,573 A * 3/1976 Chapel ................ A61M 16/009
                                                    128/205.27
5,590,644 A * 1/1997 Rosenkoetter .... A61M 16/1045
                                                    128/201.13
(Continued)

FOREIGN PATENT DOCUMENTS

BR    PI0509640 A    9/2007
BR    PI0511674 A    1/2008
BR    MU8601834-5 U    4/2008

OTHER PUBLICATIONS

C. N. Neto, MD, PhD, et al., "Use of Volatile Anesthetics During Cardiopulmonary Bypass: A Systematic Review of Adverse Events", Journal of Cardiothoracic and Vascular Anesthesia, vol. 28, No. 1, Feb. 2014; pp. 84-89.

(Continued)

*Primary Examiner* — Frank Lawrence
(74) *Attorney, Agent, or Firm* — Blank Rome LLP

(57) ABSTRACT

Improvements introduced in adsorption filter for inhaled halogenated anesthetics for cardiopulmonary bypass. It relates to an adsorption filter (10) of the type pertaining to the field of medical devices, more specifically, used to adsorb inhaled halogenated anesthetics that are eliminated through the output of the membrane oxygenators (20) of the cardiopulmonary bypass circuit (CPB); said filter (10) contains a hollow reservoir (11) for preservation of adsorber elements (ED) of the activated charcoal type (30), said reservoir (11) being of tubular cylindrical form, and it receives on one of the free extremities (11*a*) a cover (12) whose internal diameter (d1) is greater than the external diameter (d2) of the cylindrical reservoir (11), so as to produce an access chamber (C1) for the input of the inhaled anesthetic (AI) that, in turn, penetrates through a tubular member (12*a*) in the central portion of the cover (12), where (Continued)

a tube (Tb1) for connection with the oxygenator device (20) is installed.

18 Claims, 3 Drawing Sheets

(52) U.S. Cl.
CPC .... *B01D 2253/102* (2013.01); *B01D 2257/20* (2013.01); *B01D 2257/2066* (2013.01); *B01D 2259/4533* (2013.01)

(58) Field of Classification Search
CPC ... B01D 2257/2066; B01D 2259/4533; A61M 1/1698
USPC .............................. 96/108, 147; 128/205.27
See application file for complete search history.

(56) References Cited

U.S. PATENT DOCUMENTS

| | | |
|---|---|---|
| 2003/0185735 A1 | 10/2003 | Hotta et al. |
| 2009/0101010 A1* | 4/2009 | Fuesting ............. A61M 16/009 95/93 |
| 2012/0325213 A1* | 12/2012 | Orr ..................... A61M 16/009 128/205.12 |

OTHER PUBLICATIONS

S. G. De Hert, M.D., Ph.D, et al., "Cardioprotective Properties of Sevoflurane in Patients Undergoing Coronary Surgery with Cardiopulmonary Bypass Are Related to the Modalities of Its Administration", Anesthesiology, 2004 American Society of Anesthesiologists, Inc., vol. 101, No. 2, Aug. 2004; pp. 299-310.
Vapor-Clean; Dynasthetics, 1 page.
N.G. Jeffs, et al., "A new use for the 'Aldasorber'", p. 291.
N. Birgenheier, MD, et al., "Activated Charcoal Effectively Removes Inhaled Anesthetics from Modern Anesthesia Machines", Anesthesia Patient Safety Foundation, www.anesthesia-analgesia. org; Jun. 2011, vol. 12, No. 6, pp. 1363-1370.
"Activated Charcoal to Prepare an Anesthesia Machine for the Susceptible Patient", Associated Health Systems, Inc., 2 pages.

* cited by examiner

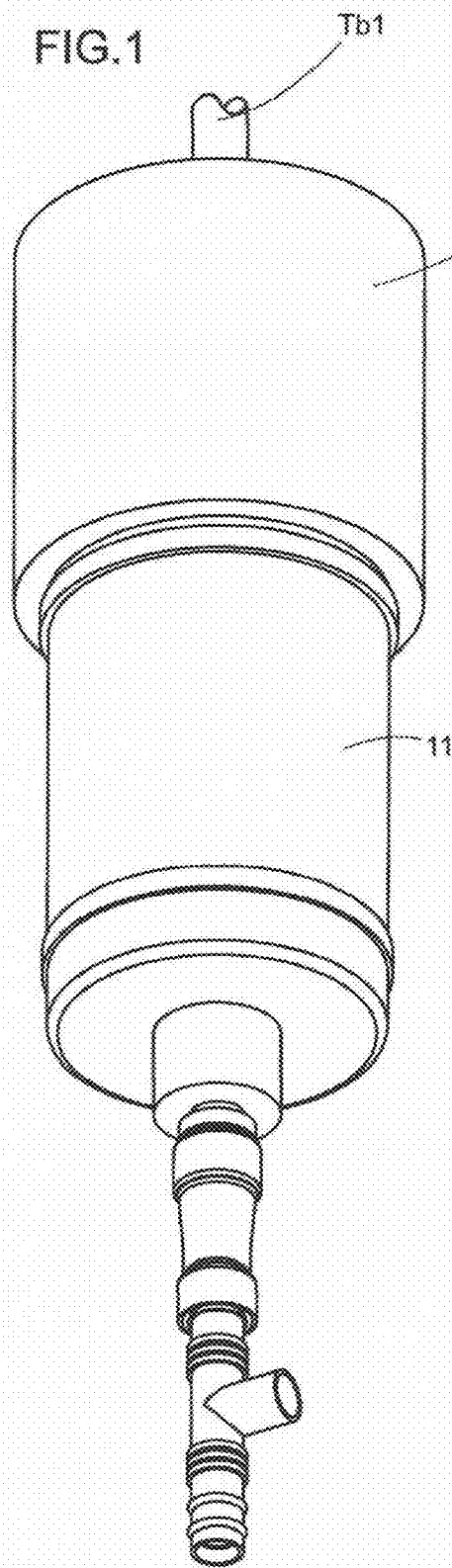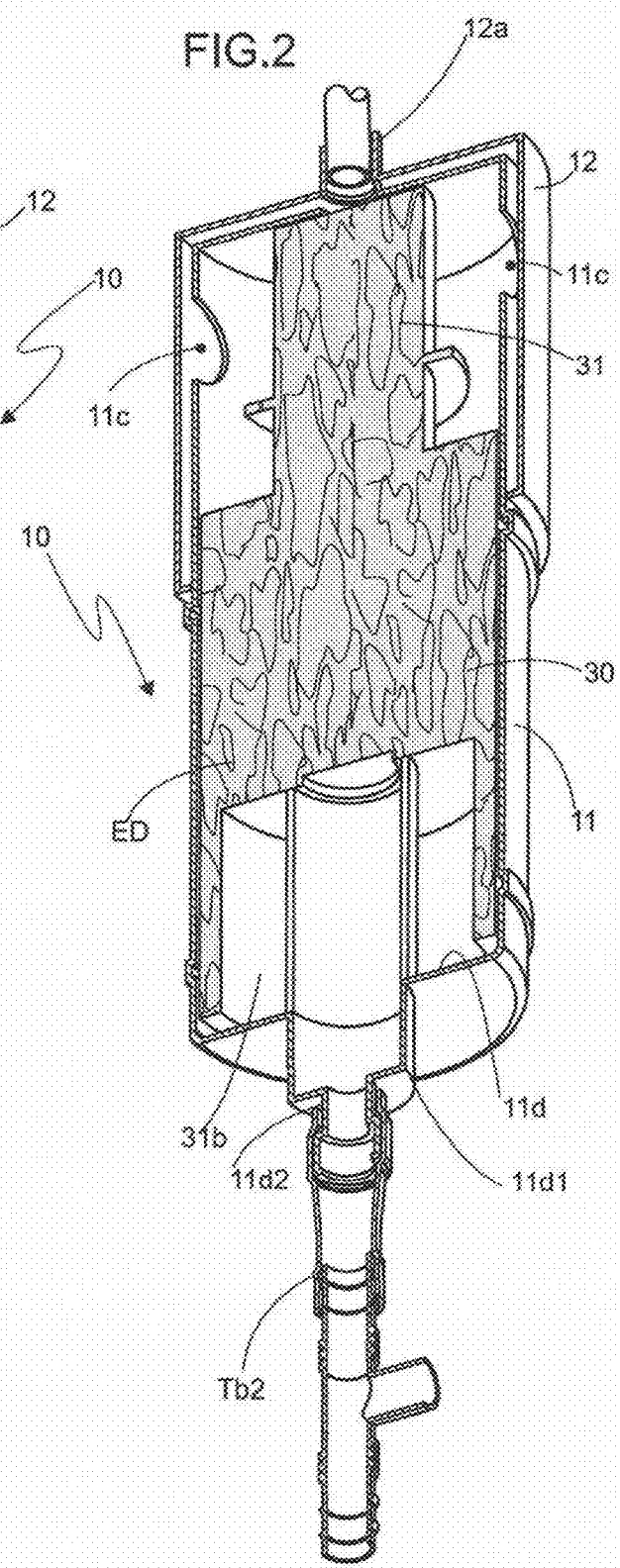

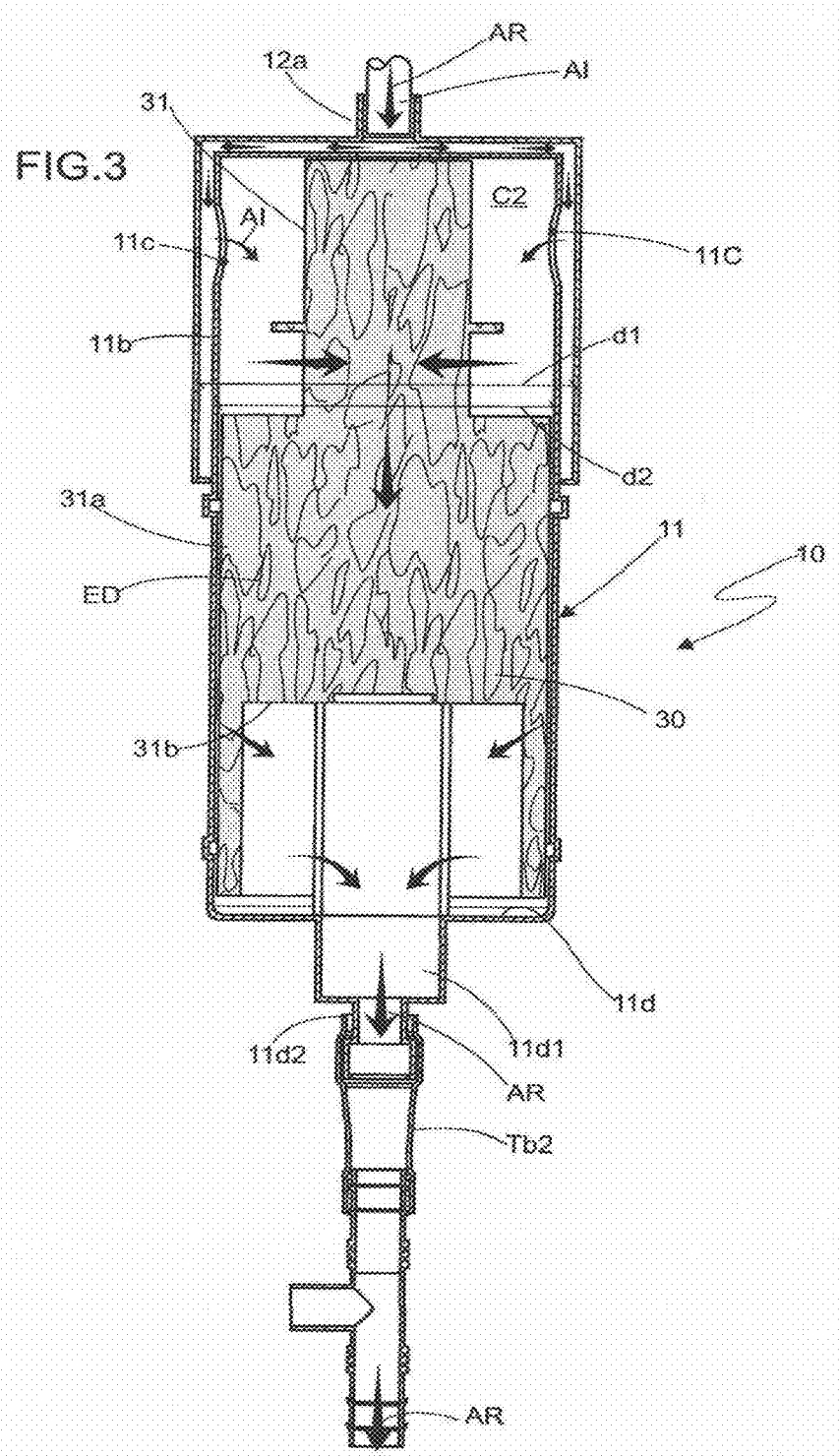

INTRODUCED IN ADSORPTION FILTER FOR INHALED HALOGENATED ANESTHETICS FOR CARDIOPULMONARY CIRCULATION BYPASS

CROSS REFERENCE TO RELATED APPLICATION(S)

This application claims priority to Brazilian Patent Application No. 1020150220170, filed on Sep. 9, 2015, which is hereby incorporated herein by reference in its entirety.

TECHNICAL FIELD OF THE INVENTION

The present invention relates to improvements introduced in an adsorption filter for inhaled halogenated anesthetics for cardiopulmonary bypass, where, notably, said filter pertains to the field of medical devices, more specifically, used to adsorb inhaled halogenated anesthetics that are eliminated through the output of the membrane oxygenators of the cardiopulmonary bypass circuit, said innovative filter showing innovative constructive characteristics that facilitate installation and use, so as to avoid pollution of the operating room as well as in the environment.

BACKGROUND OF THE INVENTION

Inhaled anesthetics are the agents most used for general anesthesia, mainly due to fast action, ease of administration and monitoring and relative reduced cost, the administration route of the anesthetic consisting of the respiratory device and accomplished by means of gases or powerful volatile liquids, such as the halogen derivative of alkane called fluothane and the halogen derivatives of ether, especially enflurane, as well as malodorous isoflurane, even, more volatile and equally malodorous desflurane, among others.

Recently, evidence of reduced mortality according to the use of volatile agents during heart surgery has led to an increase in the use of inhaled anesthetics.

The process of vaporization of the anesthetic agent in the cardiopulmonary bypass (CPB) is accomplished through a calibrated vaporizer connected to the circuit after the mixer responsible for outputting fresh gases—oxygen and compressed air, where the flow of fresh gases enters the vaporizer and, as the desired concentration is adjusted, the inhaled anesthetic is mixed with the flow of fresh gas, it being vaporized in the circuit up to the membrane oxygenator.

Currently, anesthesia devices comprise components like gas conduction system, vaporizer(s), fan, antipollution system and different monitors that evaluate the physiological function of the anesthetized individual. This integration simultaneously allows monitoring the flow of inhaled and exhaled gases, pressures, volumes and respiratory capacities with compensation of possible losses, besides the current, voltage and amperage of the electric power.

It happens that, even with all safety in the use of inhaled anesthetics, anesthesia devices can develop defects that lead to releasing a percentage of inhaled anesthetics into the atmosphere, initiating pollution in the operating room that promotes contamination of the medical and paramedical team, as well as promoting pollution of the environment. Moreover, the antipollution systems currently used for inhaled anesthetics during cardiopulmonary bypass constitute exhaust systems connected to the membrane oxygenator that, besides causing a negative pressure that can damage the oxygenator membrane, can also cause pollution of the environment, since these gases are eliminated into the atmosphere.

Anesthetic gases like isoflurane, desflurane and sevoflurane are "greenhouse gases," that is, very aggressive, with a ton of desflurane, for example, being equivalent to the pollution of 3766 tons of carbon dioxide.

To remove anesthetic gases, documents referring to filters or means of retention of inhaled halogenated anesthetic gases were found in the prior art, such as document No. BRMU8601834, which deals with an air filter applied to the expiratory valve in an anesthesia device, for which the air flow expelled by the anesthetized patient is deviated, having the objective of retaining traces of the substances administered, mainly the anesthetic agent, transforming this contaminated air into pure and unpolluted air, which does not attack the environment and does not cause illness to the people present, said filtering element being connected to the output valve of the anesthesia device or in the fan module of the same.

Document No. PI 0509640-5 deals with a system and method for removal of carbon dioxide and carbon monoxide from gas exhaled by the patient during anesthesia. The exhaled gases are dried using nonreactive desiccant to remove water, passed through a filter capable to remove particles bigger than 0.3 microns, passed through a bed comprising natural or synthetic molecular sieves capable of removing carbon dioxide and carbon monoxide and then retaken into the respiratory circuit for recirculation to the patient.

Document No. PI 0511674-0 deals with a detector that monitors the presence of halogenated agents and the presence of N20 and includes a base to which a filter canister is removably connected. The canister has an input to accept exhalant from a patient or an anesthesia machine and an output to send the filtered exhalant as gases to the base. The filtered gases are sent to a gas measurement and monitoring cell lodged in the base. The cell has a system for sensing halogenated agents and a system for sensing N20. When the filter material in the filter canister can no longer filter halogenated agents, the agents are passed from the filter to the measurement cell, which will detect the presence of the halogenated agents. An audible alarm sounds when halogenated agents are detected. This shows the user that it is time to replace the filter canister. If N20 is used, its presence is detected by the N20 sensor in the measurement cell. If N20 is detected, an audible alarm sounds to inform the user that N20 is present and that the user must carry through appropriate preventive steps.

Document No. US2003185735 refers to a process and a device for treatment of a residual anesthetic gas containing a volatile anesthetic and nitrous oxide discharged from an operating room through introduction of the gas into a adsorption cylinder with an adsorbent, where the volatile anesthetic contained in the residual anesthetic gas is adsorbed and in this way removed, and successively introducing the gas inside a catalyst layer filled with a nitrous oxide decomposition catalyst, where the nitrous oxide is decomposed into oxygen and nitrogen. Using the process and the device for treatment of residues of an anesthetic gas of the present invention, a volatile anesthetic having a possibility of destroying the ozone layer or of nitrous oxide as a global warming gas can become harmless, preventing release into the atmosphere.

The documents cited in the paragraphs above, although pertaining to the same field of application, that is, means of filtering anesthetic gases, do not present any of the characteristics of the now improved object, thus guaranteeing that the same meets the legal requirements of patentability.

OBJECT OF THE INVENTION

Thus, it is the object of the present invention to present a filter capable of adsorbing inhaled halogenated anesthetics that are eliminated through the output of the membrane oxygenators of the cardiopulmonary bypass circuit, in order to avoid pollution of the operating room and harmful effects that these anesthetic agents can cause to the health of the people who work in the surgical room and in other sections of the hospital, besides reducing pollutants to the environment.

Therefore, a study was carried out starting from construction of a prototype that can be described briefly:

For the test, an in vitro oxygenator was used in a single passage circuit. A pool of fresh bovine blood was used to carry out the system and the extracorporeal circuit with a flow route to move the blood to the tested provisional oxygenator.

The prototype filter was connected to the membrane oxygenator in the exhaled gases output portion, assuring that there were no leaks between them. The O2(%), CO2 (mmHg) and sevoflurane (%) were measured with a gas analyzer just after the prototype filter in the gas output portion (see FIG. 4). The pressures of the input (Pi) and output (Po) passages of the oxygenator were monitored with appropriately calibrated transducers connected to a pressure monitor to calculate the pressure drop (PD), Pi−Po=PD.

The blood was kept at 37±1° C. throughout the test. The conditioned blood was pumped through the membrane oxygenator, with the predetermined combinations of test variables—blood flow rate=6 l/min, gas flow speed=6 L/min, with a FiO2=100%, mixed with vaporized sevoflurane 3% concentration—for three hours.

The result was that sevoflurane was not detected in the gas analyzer, and no statistical difference was observed in the pressure drop during the test.

In this way, it is concluded that the filter is considered adequate to completely adsorb the sevoflurane and not to cause an overpressure for the membrane oxygenator during the test.

References: (1) De Hert S G. Cardioprotective properties of sevoflurane in patients subjected to coronary surgery with cardiopulmonary bypass are related to the modalities of its administration. *Anesthesiology* 2004; 101:299-310. (2) Nigro Neto, C. The use of volatile anesthetics during cardiopulmonary bypass: a systematic review of adverse events. *J Vasc Cardiothorac Anesth* 2014; 28:84-89.

DESCRIPTION OF THE FIGURES

To complete the present description in order to get a better understanding of the characteristics of the present invention and in accordance with one preferred embodiment of the same, the description is accompanied by the attached set of drawings, where, merely by way of example, its functioning is represented:

FIG. 1 represents a perspective view of the now innovative filter;

FIG. 2 shows a perspective view and partial cross-section of the filter in question;

FIG. 3 illustrates a view of the filter in longitudinal cross-section; and

DESCRIPTION OF THE INVENTION

Figure 4:
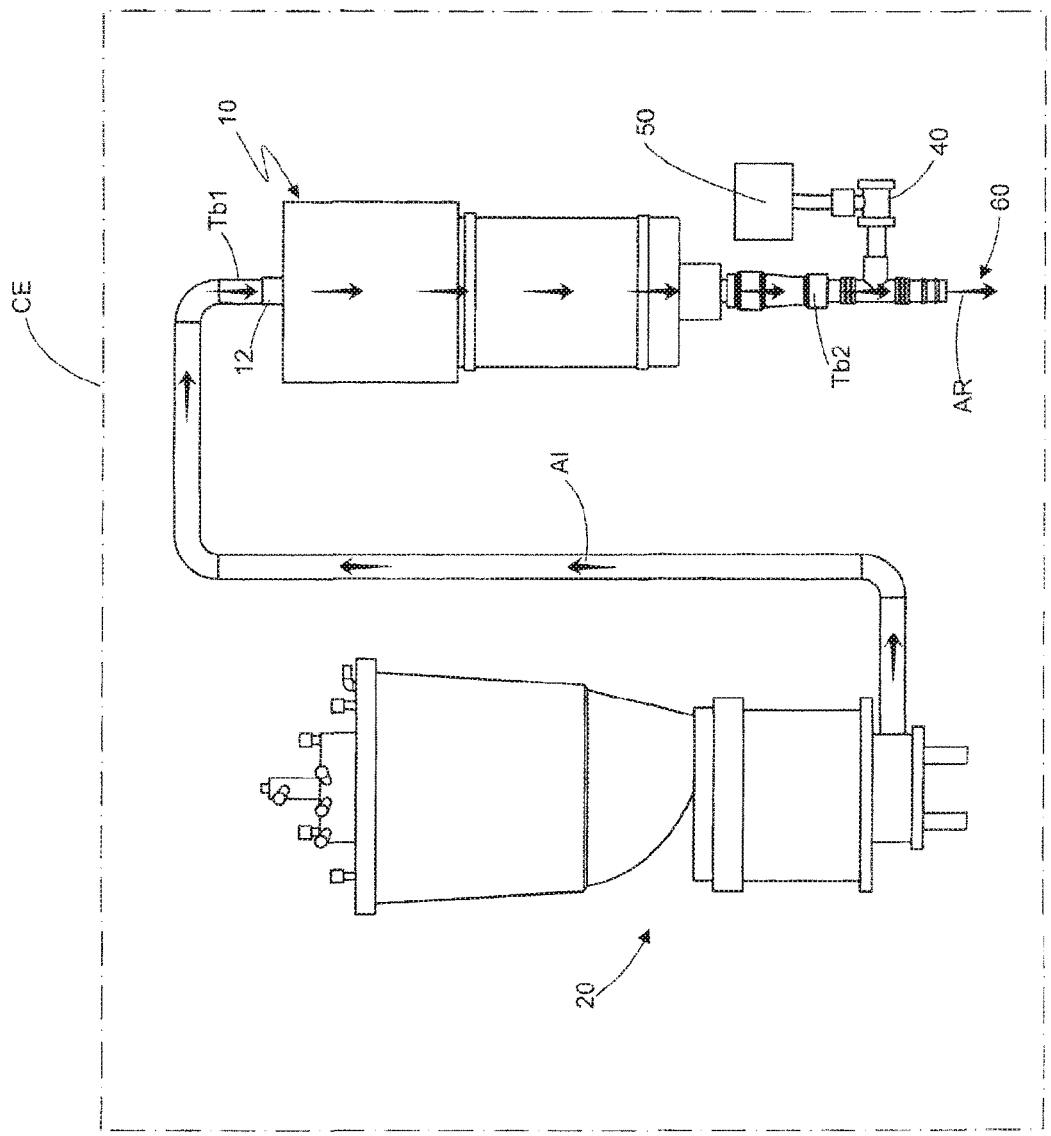
FIG. 4 discloses a schematic view of the application of the filter in question in a test.

With reference to the illustrated drawings, the present invention patent relates to "IMPROVEMENTS INTRODUCED IN ADSORPTION FILTER FOR INHALED HALOGENATED ANESTHETICS FOR CARDIOPULMONARY BYPASS." More precisely, it relates to an adsorption filter (10) of the type pertaining to the field of medical devices, more specifically, used to adsorb inhaled halogenated anesthetics that are eliminated through the outlet gases of the membrane oxygenators (20) of the cardiopulmonary bypass circuit (CPB).

According to the present invention, said filter (10) comprises hollow reservoir (11) for the preservation of adsorber elements (ED), preferably of the activated charcoal type (30), said reservoir (11) being of tubular cylindrical form, and it receives on one of the free extremities (11a) a cover (12) whose internal diameter (d1) is greater than the external diameter (d2) of the cylindrical reservoir (11), so as to produce an access chamber (C1) for the input of the inhaled anesthetic (AI) that, in turn, penetrates through a tubular member (12a) in the central portion of the cover (12), where a tube (Tb1) for connection with the oxygenator device (20) is installed, said tube (Tb1) allowing the input of the gas (AI) into the filter (10) for decontamination.

On the same extremity (11a) and in the peripheral wall (11b) are made openings (11c) intended for the input of the inhaled anesthetic (AI) after input in the chamber (C1), initiating the ingression in the chamber (C2) of the cylinder (11) endowed with adsorber element (ED).

Said element (11d) is arranged along the reservoir (11) and has a funnel-shaped portion (31) disposed next to the internal face of the extremity (11a), said funnel-shaped portion (31) having a diametrical enlargement (31a) so as to occupy the whole internal portion of the reservoir (11), proceeding to reach the base (11d). Said enlargement (31a) has a recess (31b).

Said base (11d) of the reservoir (11) has a short tubular projection (11d1) from which develops a tubular member (11d2) for installation of another tube (Tb2) that, in turn, has an inverted "T" [luer lock] connection (40) intended to deviate the filtered gas (AR) to the gas reader (50).

The filtered air (AIR) goes along the tube (Tb2) up to the exhaust system (60) and finally to the environment.

The quantity of activated charcoal (30) present in the interior of the filter (10) directly affects the efficiency and the useful time of the capacity to adsorb greater quantities of the inhaled anesthetic (AI) used, thus, the greater the dimension of the filter (10), the greater the capacity of the filtering agent (30) to adsorb greater quantities of these gases.

The tubular form of the reservoir (11), as well as the passage of the gases (AI) in the interior, produce greater dispersion of the gases and, consequently, greater utilization of contact of the gases (AI) with the activated charcoal (30).

It is certain that when the present invention is put into practice, modifications could be introduced with respect to certain details of construction and form, without this implying deviating from the basic principles that are clearly substantiated in the claims framework, it thus being understood that the terminology employed was not for the purpose of limitation.

The invention claimed is:

1. An adsorption filter for adsorbing inhaled halogenated anesthetics that are eliminated through the outlet gases of an oxygenator device, the filter comprising:
   a hollow reservoir comprising a first end and a second end, the reservoir capable of housing at least one adsorber element in an interior of the reservoir for decontaminating inhaled halogenated anesthetics, wherein the reservoir has an external reservoir diameter; and
   a cover for covering the first end of the reservoir, wherein the cover has an internal cover diameter which is greater than the external reservoir diameter such that an access chamber is formed between the cover and the reservoir, and wherein the access chamber receives input of the inhaled halogenated anesthetics that are received through an opening in a top of the cover.

2. The filter of claim 1, wherein a capacity for adsorption of a quantity of inhaled anesthetic is proportional to dimensions of the filter, which allow for a sufficient quantity of the at least one adsorber element housed within the reservoir to adsorb the inhaled halogenated anesthetics.

3. The filter of claim 1, wherein the reservoir allows for the passage of the inhaled halogenated anesthetics through the interior of the reservoir, whereby the at least one adsorber element is capable of coming into contact with the inhaled halogenated anesthetics within the interior of the reservoir.

4. The filter of claim 1, wherein the at least one adsorber element comprises activated charcoal.

5. The filter of claim 1, wherein the reservoir comprises a cylindrically tubular portion.

6. The filter of claim 1, wherein the opening of the cover is positioned within a central portion of the cover.

7. The filter of claim 1, further comprising a tube which is in communication with the opening of the cover, wherein the inhaled halogenated anesthetics enter the filter via the tube.

8. The filter of claim 1, wherein the opening of the cover is in communication with a tube for connection with an oxygenator device, wherein the tube is capable of transporting the inhaled halogenated anesthetics from the oxygenator device to the reservoir via the opening of the cover.

9. The filter of claim 1, wherein the oxygenator device comprises a membrane oxygenator device.

10. The filter of claim 1, wherein the reservoir comprises at least one aperture which is positioned between and allows for communication between the access chamber and the interior of the reservoir, thereby allowing the inhaled halogenated anesthetics within the access chamber to enter the interior of the reservoir via the at least one aperture.

11. The filter of claim 10, wherein the at least one aperture is positioned on a side wall of the reservoir.

12. The filter of claim 1, wherein the at least one adsorber element comprises a first diameter portion adjacent the first end of the reservoir, and a second diameter portion adjacent a central portion of the reservoir, wherein the central portion is positioned between the first and second ends of the reservoir, wherein the second diameter portion is larger than the first diameter portion.

13. The filter of claim 12, wherein the second diameter portion of the at least one adsorber completely fills a cross-section of the interior of the reservoir.

14. The filter of claim 1, wherein an end of the at least one adsorber element facing the second end of the reservoir comprises a recess.

15. The filter of claim 1, wherein the second end of the reservoir comprises an outlet configured to allow exit of filtered gas from the reservoir.

16. The filter of claim 15, wherein the reservoir further comprises a tubular projection in communication with the outlet.

17. The filter of claim 15, further comprising an exit tube, wherein the outlet is in communication with the exit tube which comprises or is in communication with an inverted "T" connection configured to deviate a portion of the filtered gas for transport to a gas reader.

18. The filter of claim 17, wherein a remaining portion of the filtered gas which is not deviated by the inverted "T" connection is transported via the inverted "T" connection to an exhaust system.

* * * * *